United States Patent
Baba

(10) Patent No.: US 12,109,052 B2
(45) Date of Patent: Oct. 8, 2024

(54) RADIOGRAPHIC IMAGING DEVICE AND RADIOGRAPHIC TREATMENT DEVICE

(71) Applicant: Hitachi High-Tech Corporation, Tokyo (JP)

(72) Inventor: Rika Baba, Tokyo (JP)

(73) Assignee: HITACHI HIGH-TECH CORPORATION, Tokyo (JP)

(*) Notice: Subject to any disclaimer, the term of this patent is extended or adjusted under 35 U.S.C. 154(b) by 242 days.

(21) Appl. No.: 17/642,257

(22) PCT Filed: Jun. 4, 2020

(86) PCT No.: PCT/JP2020/022060
§ 371 (c)(1),
(2) Date: Mar. 11, 2022

(87) PCT Pub. No.: WO2021/053891
PCT Pub. Date: Mar. 25, 2021

(65) Prior Publication Data
US 2022/0313180 A1    Oct. 6, 2022

(30) Foreign Application Priority Data
Sep. 20, 2019   (JP) ................. 2019-171361

(51) Int. Cl.
*A61B 6/03*      (2006.01)
*A61B 6/04*      (2006.01)
*G06T 11/00*     (2006.01)

(52) U.S. Cl.
CPC .......... *A61B 6/032* (2013.01); *G06T 11/003* (2013.01); *A61B 6/0407* (2013.01)

(58) Field of Classification Search
CPC ..... A61B 6/032; A61B 6/0407; A61B 6/5264; A61B 6/022; A61B 6/5288; A61B 6/541;
(Continued)

(56) References Cited

U.S. PATENT DOCUMENTS 4,868,747 A    9/1989   Mori et al.
6,865,248 B1*  3/2005   Rasche ............... A61B 6/541
                                                378/4
(Continued)

FOREIGN PATENT DOCUMENTS

DE    37 51 690 T2    8/1996
JP    06-269445 A     9/1994
(Continued)

OTHER PUBLICATIONS

Translation of JP-2008228828 (Year: 2008).*
(Continued)

*Primary Examiner* — Dani Fox
*Assistant Examiner* — Soorena Kefayati
(74) *Attorney, Agent, or Firm* — MATTINGLY & MALUR, PC

(57) ABSTRACT

Artifacts in a tomographic image of a subject including a cyclically moving object to be treated are reduced. A radiographic imaging device includes: a gantry that is equipped with two sets of radiation sources and detectors which are used in pairs, the gantry rotating the radiation sources and the detectors around a subject; and a reconstruction section that reconstructs a tomographic image of the subject based on multiple projection images generated from output of the detectors. The radiographic imaging device further includes: a phase calculation section; a divide section that divides, on a phase-by-phase basis, first projection image groups of multiple projection images acquired by the first set, and similarly second projection image groups acquired by the second set; and a condition setting section. The reconstruction section reconstructs a tomographic image by use of the first and second projection image groups that are placed in the same phase.

10 Claims, 8 Drawing Sheets

(58) Field of Classification Search
CPC .... A61B 6/488; A61N 5/1068; A61N 5/1037; A61N 5/1082; A61N 5/1081; A61N 5/1049; A61N 2005/1061; G06T 11/003; G06T 11/005
See application file for complete search history.

(56) References Cited

U.S. PATENT DOCUMENTS

| | | | | |
|---|---|---|---|---|
| 2007/0025509 A1* | 2/2007 | Pang | | A61B 6/025 378/65 |
| 2007/0189436 A1* | 8/2007 | Goto | | A61B 6/4085 378/4 |
| 2008/0130829 A1* | 6/2008 | Bruder | | A61B 6/5264 378/92 |
| 2009/0242776 A1* | 10/2009 | Kobashi | | A61B 6/037 250/363.04 |
| 2009/0283682 A1* | 11/2009 | Star-Lack | | A61B 6/4441 250/363.1 |
| 2010/0142670 A1* | 6/2010 | Saito | | A61B 6/032 378/8 |
| 2012/0275657 A1* | 11/2012 | Kolthammer | | A61B 6/037 382/107 |
| 2012/0278055 A1* | 11/2012 | Schweizer | | A61B 6/5264 703/11 |
| 2012/0292534 A1* | 11/2012 | Geneser | | A61N 5/1069 250/492.1 |
| 2013/0165770 A1* | 6/2013 | Li | | A61N 5/1067 600/430 |
| 2014/0050297 A1* | 2/2014 | Mostafavi | | A61B 6/584 378/19 |
| 2014/0192952 A1* | 7/2014 | Keall | | A61B 6/486 378/8 |
| 2014/0275704 A1* | 9/2014 | Zhang | | A61N 5/1067 600/1 |
| 2015/0036793 A1* | 2/2015 | Umekawa | | A61B 6/541 378/8 |
| 2015/0045604 A1* | 2/2015 | Sawkey | | A61N 5/1068 600/1 |
| 2015/0243025 A1* | 8/2015 | Berlinger | | G06T 7/0012 382/128 |
| 2016/0163095 A1* | 6/2016 | Wollenweber | | A61B 6/037 382/131 |
| 2016/0174921 A1* | 6/2016 | Wikler | | A61B 6/488 378/19 |
| 2016/0175614 A1* | 6/2016 | Taguchi | | G06V 10/255 600/1 |
| 2017/0043184 A1* | 2/2017 | Mori | | A61N 5/1077 |
| 2017/0296843 A1* | 10/2017 | Taguchi | | A61N 5/1037 |
| 2019/0183447 A1* | 6/2019 | Mori | | A61B 6/463 |
| 2019/0336795 A1* | 11/2019 | Zhou | | A61N 5/1081 |
| 2020/0069967 A1* | 3/2020 | Mori | | A61N 5/1068 |

FOREIGN PATENT DOCUMENTS

| | | | |
|---|---|---|---|
| JP | 2004033471 A | * | 2/2004 |
| JP | 2004-065982 A | | 3/2004 |
| JP | 2008228828 A | * | 10/2008 |
| JP | 2015-029793 A | | 2/2015 |
| JP | 2016-120282 A | | 7/2016 |
| WO | 2005/122901 A1 | | 12/2005 |
| WO | 2018/183748 A1 | | 10/2018 |

OTHER PUBLICATIONS

Translation of JP-2004033471 (Year: 2004).*
International Search Report of PCT/JP2020/022060 dated Aug. 25, 2020.
German Office Action received in corresponding German Application No. 11 2020 003 891.2 dated Oct. 14, 2022.

* cited by examiner

FIG. 8
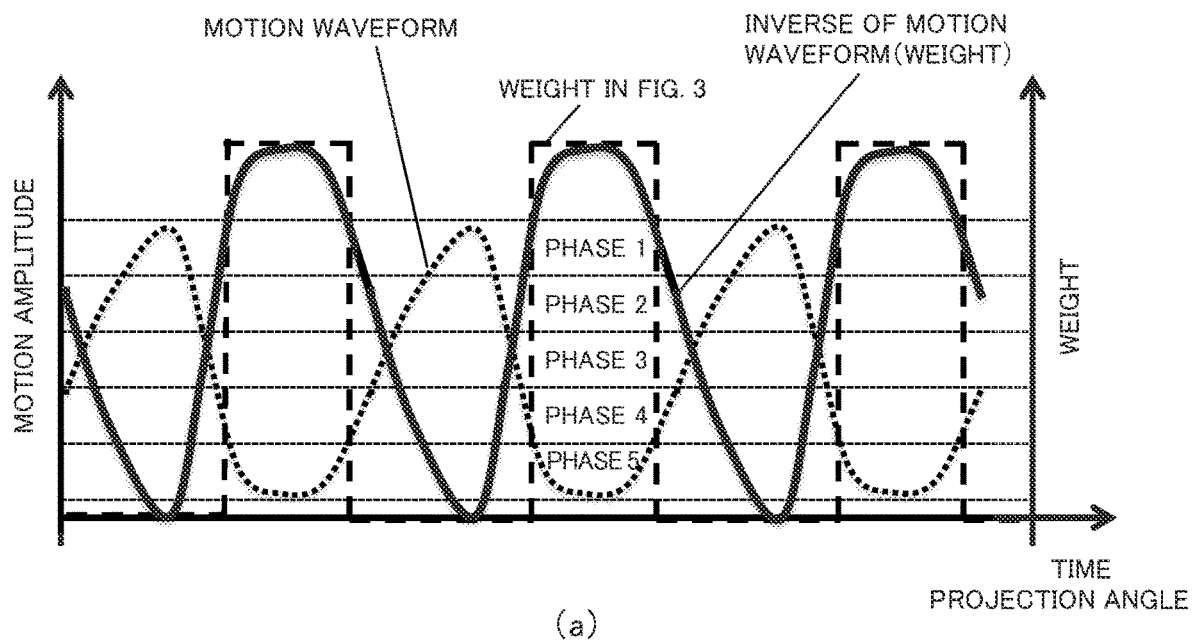
(a)
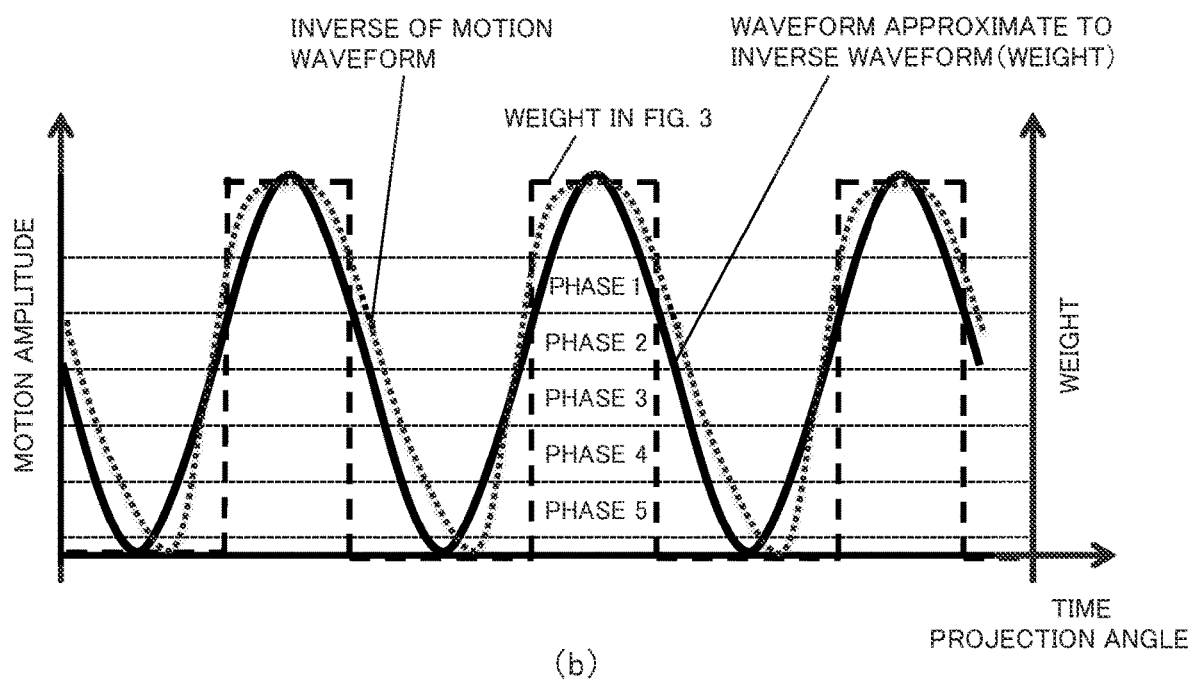
(b)

FIG. 9
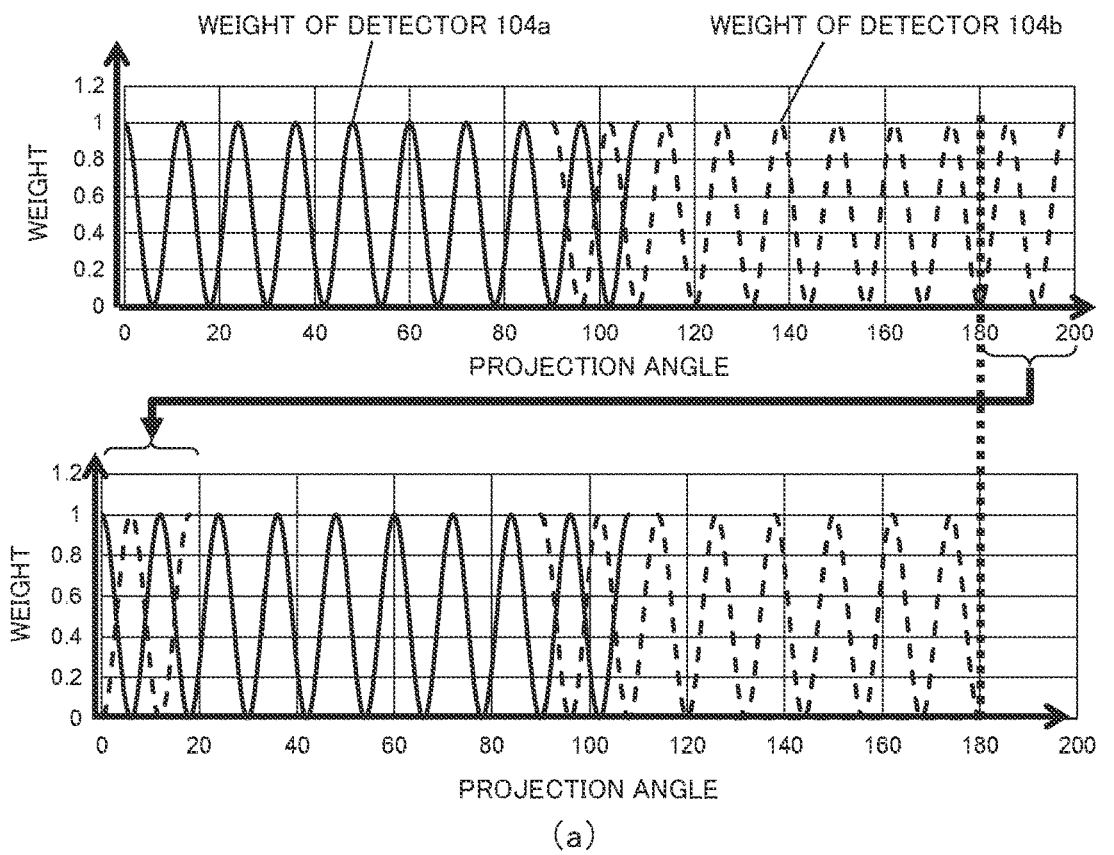
(a)
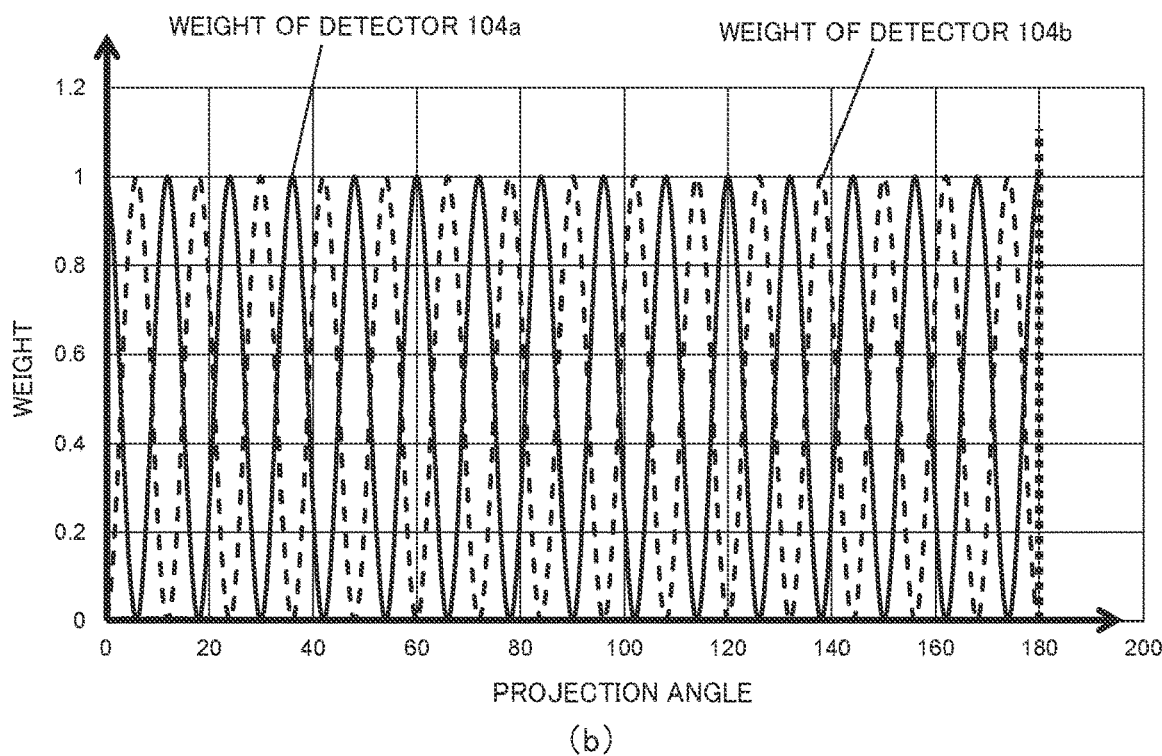
(b)

RADIOGRAPHIC IMAGING DEVICE AND RADIOGRAPHIC TREATMENT DEVICE

TECHNICAL FIELD

The present invention relates to technology for capturing a three-dimensional image of a subject and an object to be treated when the object to be treated periodically moving within the subject is treated with a radiographic treatment device and, more particularly, to technology for reducing artifacts included in a three-dimensional image.

BACKGROUND ART

For the radiographic treatment device irradiating the object to be treated such as a malignant tumor or the like with radiation, it is important to focus the radiation on the object to be treated and to minimize irradiation to normal cells. Particularly, for the object to be treated cyclically moving by breathing or the like, timing and/or a point for radiation irradiation must be precisely controlled in response to motion of the object to be treated.

PTL 1 discloses the radiographic treatment system in which the treatment radiation source and two sets of imaging devices including the X-ray source-detector pairs are mounted to the rotating support device circling the subject. In PTL 1, a three-dimensional point of the object to be treated is determined from two projection images acquired by the two sets of imaging devices, and only projection image with the object to be treated located in a specified region is used to reconstruct a tomography image or all projection images are used to reconstruct a tomographic image.

CITATION LIST

Patent Literature

PTL 1: Japanese Patent No. 6181459

SUMMARY OF INVENTION

Technical Problem

In PTL 1, however, an artifact may appear in the reconstructed tomographic image. Specifically, in the case of using only the projection image with the object to be treated located in a specified region, if the distribution of projection angles at which the projection images are acquired is biased, an artifact will appear. In the case of using all the projection images, the motion of the object to be treated will cause an artifact.

Accordingly, it is an object of the present invention to provide a radiographic imaging device and a radiographic treatment device which are capable of reducing artifacts in a tomographic image of a subject including a cyclically moving object to be treated.

Solution to Problem

To achieve the above object, an aspect of the present invention provides a radiographic imaging device that includes: a gantry that is equipped with two sets of radiation sources from which radiation is emitted to a subject and detectors that detect the radiation passing through the subject, the radiation sources and the detectors being used in pairs, the gantry rotating the radiation sources and the detectors around the subject; and a reconstruction section that reconstructs a tomographic image of the subject based on multiple projection images generated from output of the detectors. The radiographic imaging device further includes: a phase calculation section that calculates a motion phase based on cyclic motion of the subject; a divide section that divides, on a phase-by-phase basis, first projection image groups of multiple projection images acquired by the first set, and second projection image groups of multiple projection images acquired by the second set; and a condition setting section that sets imaging conditions for allowing a first projection image group of the first projection image groups and a second projection image group of the second projection image groups to implement mutual compensation for each other's spacing between projection angles, the first projection image group and the second projection image group being placed in the same phase. The reconstruction section reconstructs a tomographic image by use of the first projection image group and the second projection image group that are placed in the same phase.

Another aspect of the present invention provides a radiographic treatment device that includes the radiographic imaging device and a treatment radiation source from which treatment radiation is emitted to an object to be treated.

Advantageous Effects of Invention

According to the present invention, a radiographic imaging device and a radiographic treatment device are provided which are capable of reducing artifacts in a tomographic image of a subject including a cyclically moving object to be treated.

BRIEF DESCRIPTION OF DRAWINGS

FIG. 8 is a diagram illustrating an example of weight in Example 2.

FIG. 9 is a diagram illustrating a difference between ranges of projection angles in rotation measurement.

DESCRIPTION OF EMBODIMENTS

Embodiments of a radiographic imaging device and a radiographic treatment device according to the present invention will now be described with reference to the accompanying drawings. It is noted that throughout the following description and the accompanying drawings, like reference signs are used to indicate elements having like functional configurations for the purpose of avoiding a similar description.

Example 1

Figure 1:
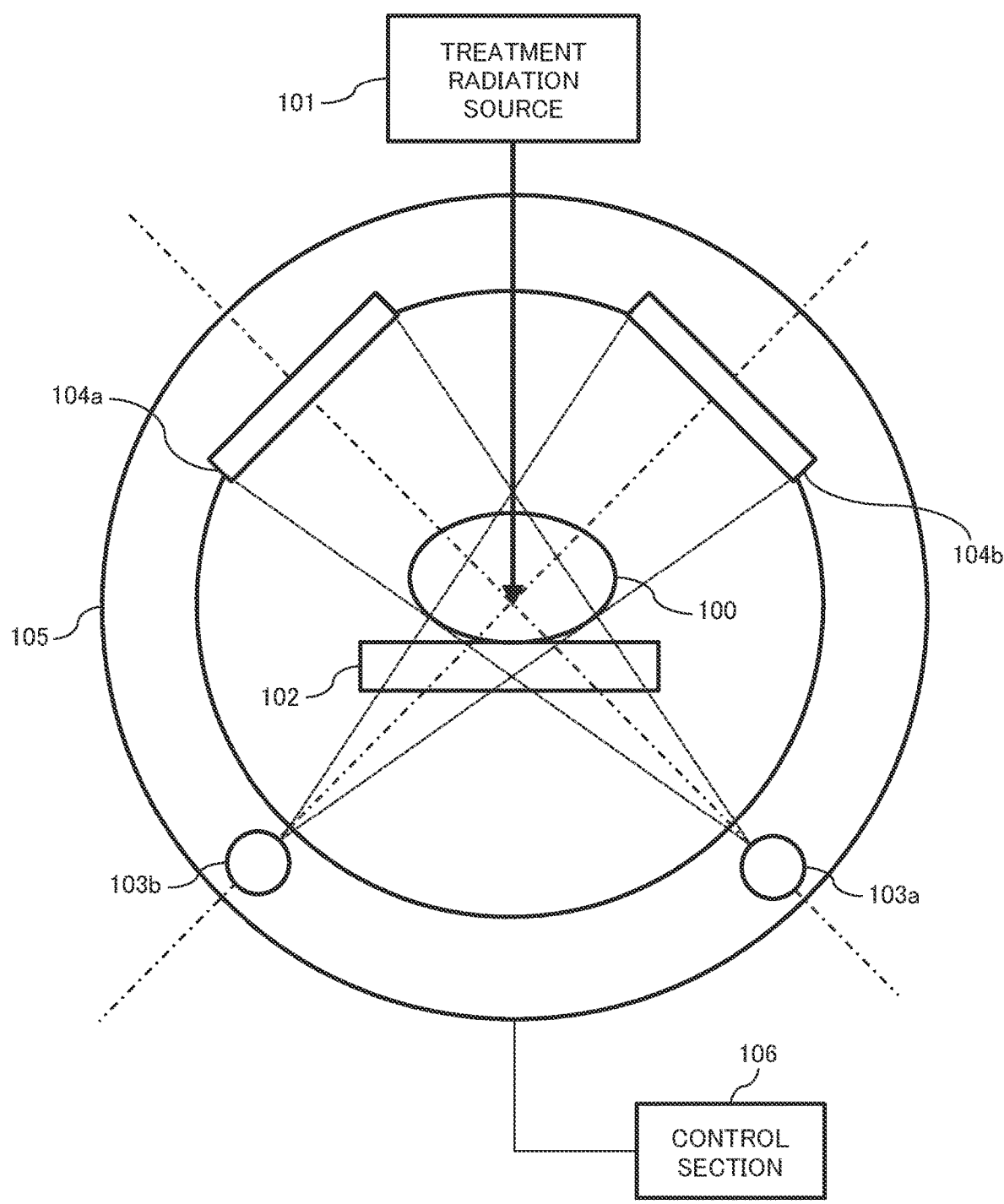
FIG. 1 is an overall block diagram illustrating a radiographic treatment device.

The overall configuration of the radiographic treatment device will be described with reference to FIG. 1. The radiographic treatment device includes a treatment radiation source 101, a bed 102, X-ray sources 103, detectors 104, a gantry 105, and a control section 106.

The treatment radiation source 101 is a device that irradiates an object to be treated within a subject 100 with treatment radiation, the subject 100 being placed on the bed 102. The treatment radiation source 101 is connected to an electron beam accelerator and/or the like. If the object to be treated moves, the treatment radiation is emitted when the object to be treated moves into an irradiation region, and/or the direction of the treatment radiation is changed to track the object to be treated. The bed 102 is a device that moves the subject 100 to a suitable position for treatment, and moves from up to down, from side to side and from front to back.

The X-ray source 103 is a device that irradiates the subject 100 with the X-rays. The detector 104 is a device that detects a two-dimensional distribution of the X ray passing through the subject 100, and is placed on the opposite side of the subject 100 from the X-ray source 103 to face this X-ray source 103. The X-ray source 103 and the detector 104 are paired with each other in order to acquire a projection image of the subject 100 so that a two-dimensional point of the object to be treated is extracted on the projection image. It is noted that in this example, two pairs, a pair of an X-ray source 103a and a detector 104a and a pair of an X-ray source 103b and a detector 104b, are provided, which therefore enables calculation of a three-dimensional point of the object to be treated from the two-dimensional points on the respective projection images acquired by the respective pairs.

The gantry 105 is a device that is equipped with the pairs of the X-ray sources 103 and the detectors 104 and rotates the X-ray sources 103 and the detectors 104 around the subject 100. The two pairs are rotated together at the same speed as each other by the gantry 105. The projection images are acquired from multiple directions by alternating between the X-ray irradiation and the detection while the X-ray sources 103 and the detectors 104 are being rotated. It is noted that an angle in the direction in which the X-rays are emitted when the projection images are acquired is referred to as a "projection angle", and a predetermined direction, for example, a direction in which the subject 100 is irradiated from directly above with the X-rays is defined as the projection angle being zero degrees. Alternatively, the gantry 105 may be equipped with three or more pairs of the X-ray sources 103 and the detectors 104 and/or may be equipped with the treatment radiation source 101.

The control section 106 is a device that controls each section of the radiographic treatment device, which is composed of a computer and/or the like. Conditions for treatment are set by an operator via an input device such as a keyboard, a mouse, a touch panel, and/or the like.

Figure 2:
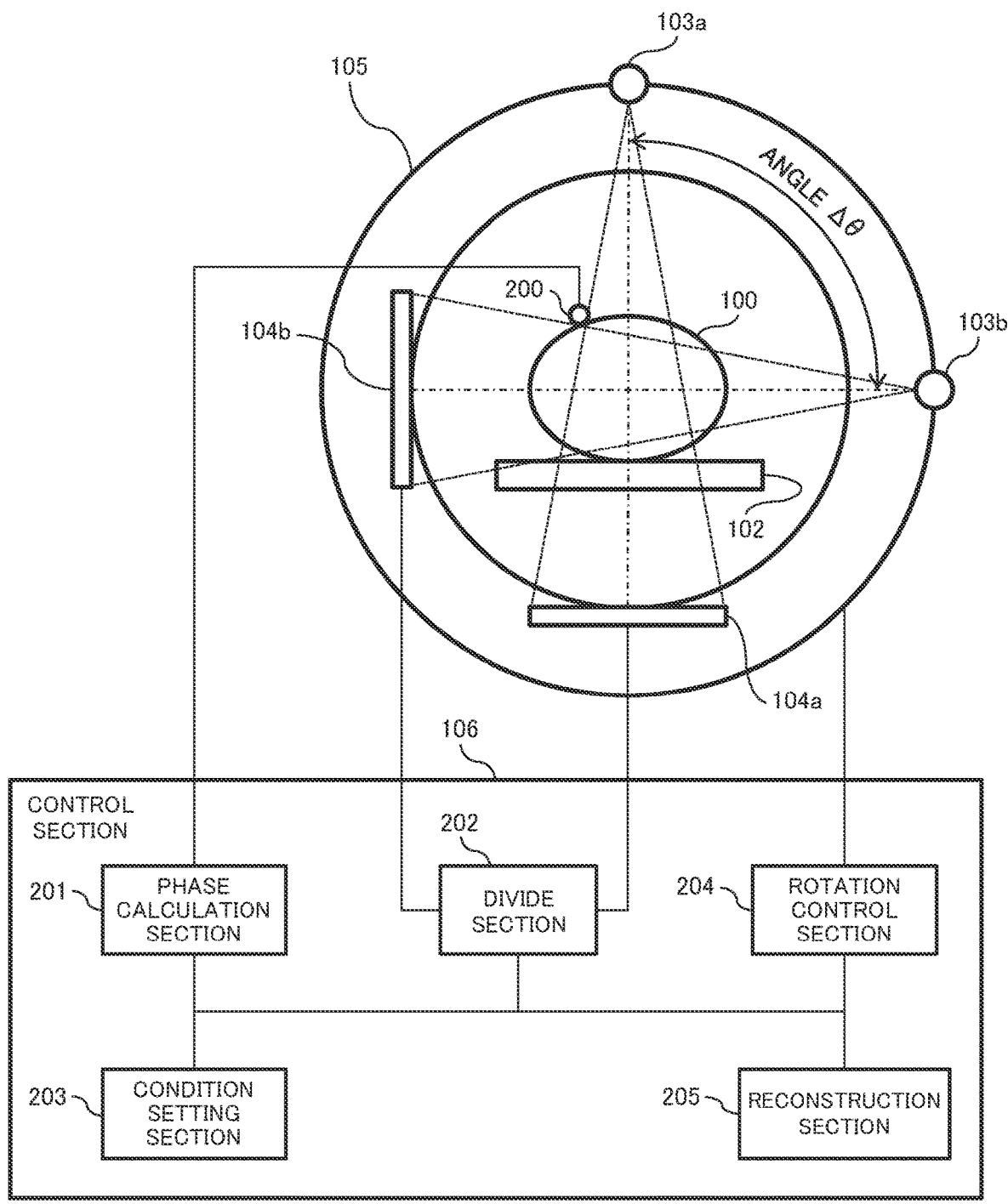
FIG. 2 is an overall block diagram illustrating a radiographic imaging device.

The overall configuration of the radiographic imaging device will be described with reference to FIG. 2. The radiographic imaging device includes the bed 102, the X-ray sources 103, the detectors 104, the gantry 105, a body motion measurement section 200, and the control section 106. The bed 102, the X-ray sources 103, the detectors 104, and the gantry 105 are configured as described in FIG. 1. It is noted that an angle formed by one pair of the X-ray source 103a and the detector 104a and the other pair of the X-ray source 103b and the detector 104b is defined as Δθ which may be a constant value, e.g., 90 degrees, alternatively, may be changed to any value other than zero and 180 degrees.

The body motion measurement section 200 is a device that measure the motion of the subject 100, in which the subject 100 is irradiated with, for example, a laser, ultrasonic waves, millimeter waves, near-infrared rays, or the like, and then a change in point of the external surface is measured based on a measured value of the laser or the like reflecting from the external surface of the subject 100. Alternatively, the body motion measurement section 200 may be a device that irradiates the subject 100 with X-rays, ultrasonic waves, magnetic fields, or the like and then measures a change on point of the internal structure of the subject 100. Stated another way, the body motion measurement section 200 measures, over time, the distances between a reference point and a point of interest of the subject 100 in order to measure the cyclic motion of the subject 100, for example, the breathing motion.

The control section 106 is a device that controls each section of the radiographic imaging device and generates various images, e.g., tomographic images, based on the output from the detectors 104, which is configured by a computer and/or the like having a CPU (Central Processing Unit), memory, and the like. The conditions for imaging are set by an operator via an input device such as a keyboard, a mouse, a touch panel, and/or the like. Alternatively, the conditions for imaging are received by the control section 106 after being set by a condition setting section 203 which will be later with reference to FIG. 2. The various images generated by the control section 106 are displayed on a display device such as a liquid crystal display and/or the like and/or stored in a storage device such as an HDD (Hard Disk Drive), an SSD (Solid State Drive), and/or the like.

The control section 106 includes a phase calculation section 201, a divide section 202, a condition setting section 203, a rotation control section 204, and a reconstruction section 205, all of which are principal parts in this example. It is noted that those principal parts may be configured by software run in the control section 106, or alternatively may be configured by dedicated hardware. In the following description, the case of the principal parts in this example being configured by software is described.

Figure 3:
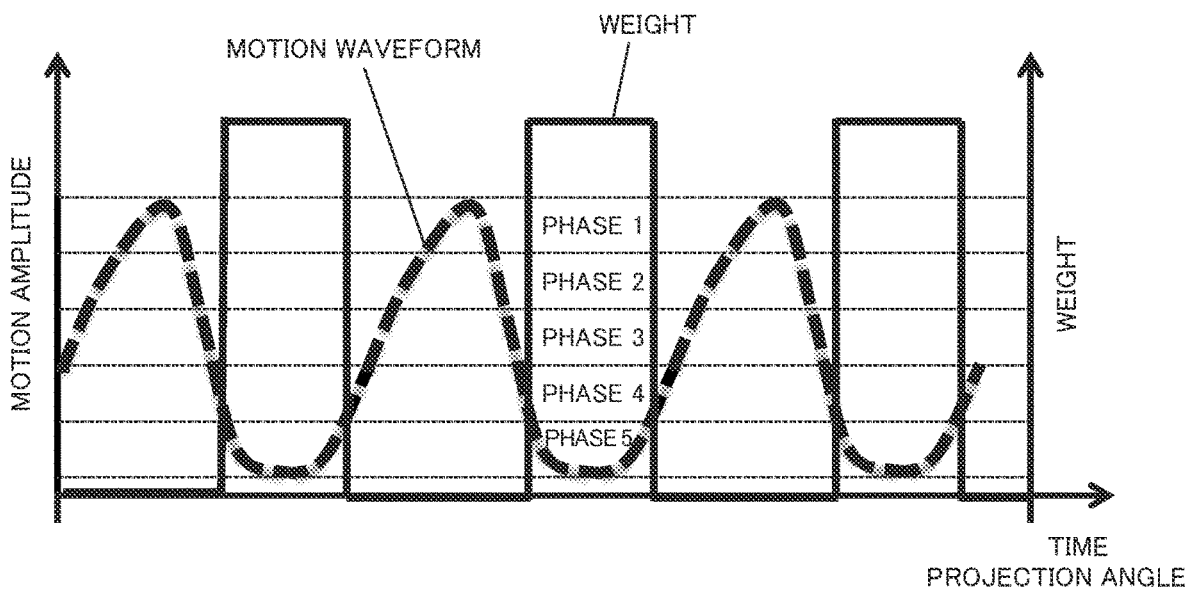
FIG. 3 is a diagram illustrating a phase calculation.

The phase calculation section 201 calculates phases of motion of the subject 100 based on the output from the body motion measurement section 200. Specifically, the amplitude of motion is divided into multiple divisions, and a phase number is assigned to each range of amplitude divisions. An example of the phase calculation is described with reference to FIG. 3. An example motion waveform is shown by the dotted line in FIG. 3. It is noted that the vertical axis represents motion amplitude at a measured point relative to any reference point and the horizontal axis represents time. In FIG. 3, the phase calculation section 201 divides the motion amplitude into five ranges, and the phase numbers are assigned in decreasing order of amplitude value, in which the smallest amplitude range is defined as Phase 5. In other words, a phase is calculated based on motion magnitude. The phase calculation section 201 also calculates a motion cycle of the subject 100.

The divide section 202 divides each of first projection image groups and second projection image groups on a phase-by-phase basis, the first projection image groups being projection image groups acquired by one pair of the X-ray source 103a and the detector 104a, the second projection image groups being projection image groups acquired by the other pair of the X-ray source 103b and the detector 104b. While the projection images are acquired at various projection angles, the subject 100 keeps on moving cyclically. Therefore, each projection image is associated with a phase of the motion of the subject 100 according to the time the projection image is acquired. That is, the multiple projection images are divided on a phase-by-phase basis according to projection angle.

Even if the subject 100 moves faster than the rotational speed of the gantry 105, the multiple projection images are divided on a phase-by-phase basis, and the projection image groups placed in the same phase are used to reconstruct a tomographic mage in order to obtain an image with reduced artifacts due to the motion of the subject 100. For example, as illustrated in FIG. 3, a weight 1.0 is assigned to the projection images placed in the projection angle corresponding to Phase 5, and a weight 0.0 is assigned to the projection images in Phase 1 to Phase 4. Thereby, the projection images in Phase 1 to Phase 4 are not used to reconstruct the tomographic image, and the projection image group in Phase 5 alone is used to reconstruct the tomographic image. However, if the distribution of projection angles at which the projection images are acquired is biased, an artifact will also appear. To address this, in this example, the imaging conditions are set such that the projection angles of the projection image groups placed in the same phase become uniform.

Figure 4:
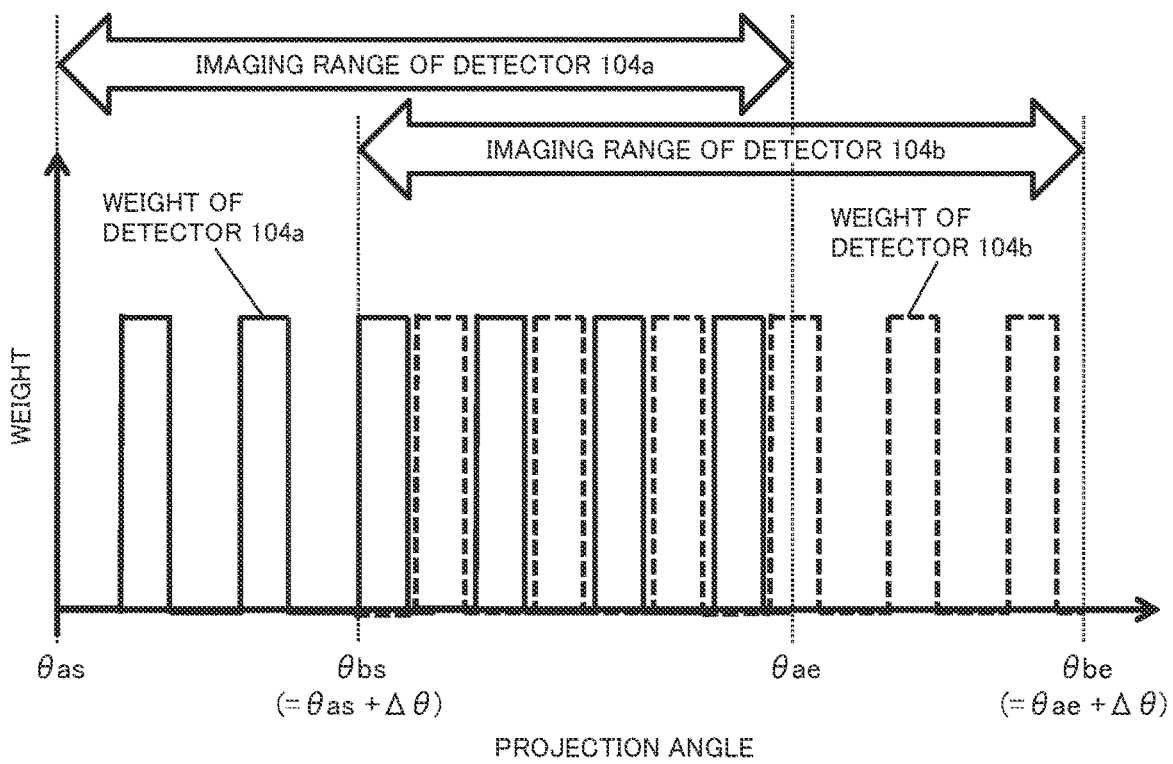
FIG. 4 is a diagram illustrating mutual compensation of projection image groups for between each other's spacing between projection angles.

The condition setting section 203 sets imaging conditions such that the first projection image group and the second projection image group, which are placed in the same phase, mutually compensate for each other's spacing between projection angles. Reference is made to FIG. 4 to describe an example of the first projection image group and the second projection image group mutually compensating for each other's spacing between projection angles. In FIG. 4, based on a certain phase, e.g., phase 5 in FIG. 3, the weight set for the first projection image group is shown by the solid lines and the weight set for the second projection image group is shown by the dotted lines. It is noted that the vertical axis represents a weight for a projection image group and the vertical axis represents a projection angle. Further, the imaging range of the detector 104a is from a first starting angle θas to a first end angle θae and the imaging range of the detector 104b is from a second starting angle θbs to a second end angle θbe, in which the two imaging ranges are out of alignment with each other by Δθ. In FIG. 4, the condition setting section 203 sets the imaging conditions such that the weights of the first projection image group and the second projection image group mutually compensate for each other's spacing between projection angles. By virtue of such settings for the imaging conditions, the projection angles of the projection image groups placed in the same phase become uniform, and thus a reduction in artifact is enabled in the tomographic image to be reconstructed.

It is noted that one of the imaging conditions set by the condition setting section 203 is a rotational speed ρ of the gantry 105 which is calculated, for example, using the following equation.

$$\rho = 2\Delta\theta / (T \cdot (2n-1)) \quad \text{(Eq. 1)}$$

where Δθ is an angle formed by one pair of the X-ray source 103a and the detector 104a and the other pair of the X-ray source 103b and the detector 104b, T is a motion cycle of the subject 100, and n is a natural number. Stated another way, the rotational speed ρ of the gantry 105 is set based on an angle formed by the two pairs of the X-ray sources 103 and the detectors 104 and a motion cycle of the subject 100.

Also, one of the imaging conditions set by the condition setting section 203 is irradiation timing t at which X rays are emitted from the X-ray source 103, which is calculated, for example, using the following equation.

$$t = 2T/(2n-1) \quad \text{(Eq. 2)}$$

That is, the X-ray irradiation timing t is set based on a motion cycle of the subject 100.

Figure 5:
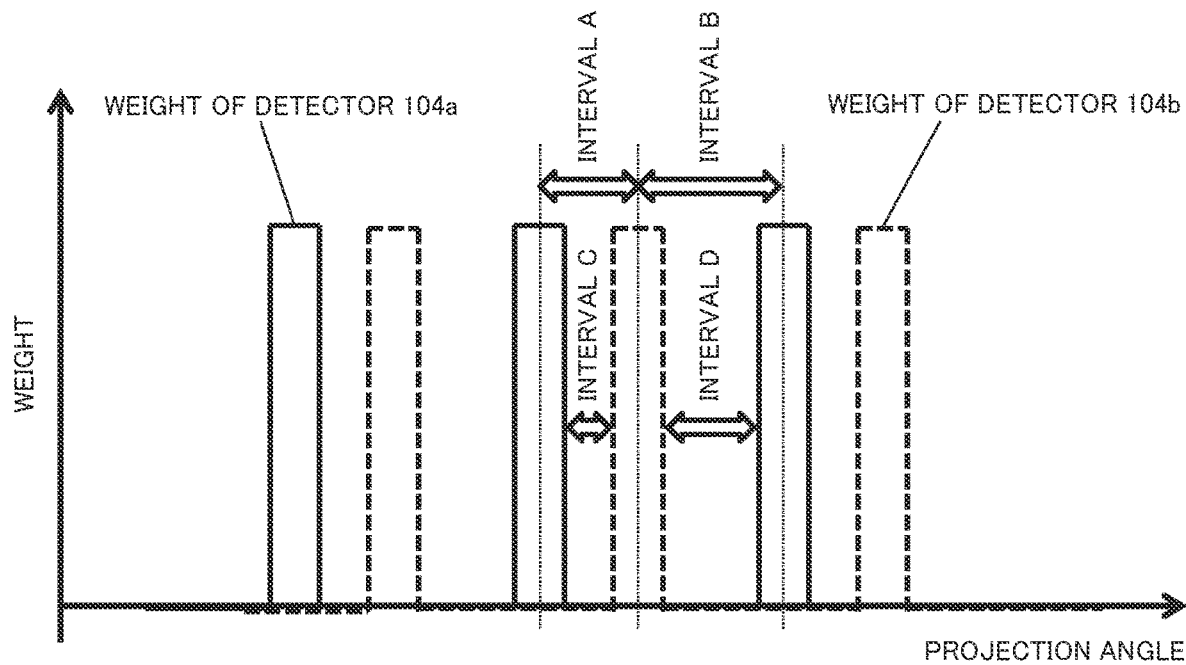
FIG. 5 is a diagram illustrating intervals between projection images.

Also, the condition setting section 203 preferably sets imaging conditions such that the first projection image group and the second projection image group, which are placed in the same phase, fill in uniform intervals or each other's spacing between projection angles. Reference is made to FIG. 5 to describe the intervals between the first projection image group and the second projection image group. In FIG. 5, similarly to FIG. 4, the weight set for the first projection image group is shown by the solid lines and the weight set for the second projection image group is shown by the dotted lines. It is noted that Interval A is an interval between the center angle of the weight 1.0 for a first projection image group and the center angle of the weight 1.0 for a second projection image group, and Interval B is an interval between the center angle of the weight 1.0 for the second projection image group and the center angle of the weight 1.0 for the subsequent first projection image group. As Interval A and Interval B are closer to the same value, the first projection image group and the second projection image group which are placed in the same phase have intervals closer to uniform intervals. Therefore, the projection angles of the projection image groups placed in the same phase becomes uniform.

In FIG. 5, also, Interval C is an interval between the end angle of the weight 1.0 for a first projection image group and the starting angle of the weight 1.0 for a second projection image group, and Interval D is an interval between the end angle of the weight 1.0 for the second projection image group and the starting angle of the weight 1.0 for the subsequent first projection image group. As Interval C and Interval D are closer to the same value, the first projection image group and the second projection image group which are placed in the same phase have intervals closer to uniform intervals. Therefore, the projection angles of the projection image groups placed in the same phase becomes uniform.

Also, as Interval C and Interval D are smaller, the spacing between projection angles of the first projection image group and the second projection image group which are placed in the same phase are increasingly filled by the each other's projection images. This enables a reduction in artifacts caused by lack of projection images. It is noted that if Interval C and Interval D take a negative value, the first projection image group and the second projection image group which are placed in the same phase partially overlap each other, and this enables a further reduction in artifacts caused by lack of projection images. Stated another way, a reduction in artifacts is enabled by setting a projection angle range for each projection image such that the first projection image group and the second projection image group which are placed in the same phase fill in each other's spacing between projection angles or partially overlap each other.

The rotation control section 204 controls the rotation of the gantry 105 according to a rotational speed that is one of the imaging conditions set by the condition setting section 203.

The reconstruction section 205 reconstructs the tomographic image by use of the first projection image group and the second projection image group which are placed in the same phase. As described above, because the first projection image group and the second projection image group, which are placed in the same phase, mutually compensate for each other's spacing between projection angles, the reconstruction section 205 reconstructs the tomographic image with reduced artifacts.

Figure 6:
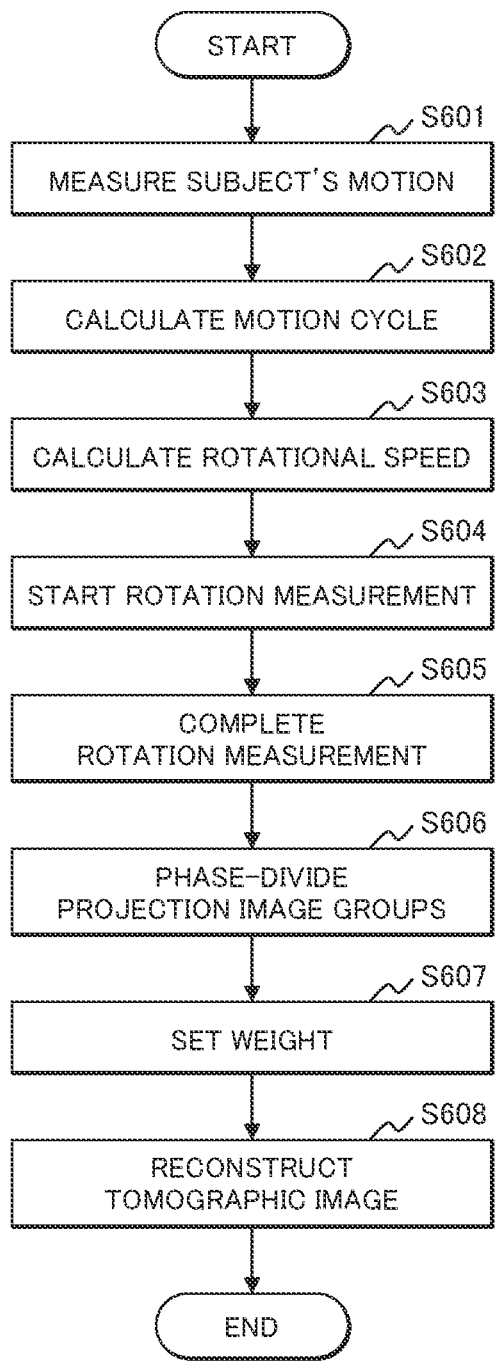
FIG. 6 is a diagram illustrating an example processing flow in Example 1.

An example processing flow executed in this example will be described with reference to FIG. 6.

(S601)

The body motion measurement section 200 measures motion of the subject 100 prior to the projection image acquisition. A measured value by the body motion measurement section 200 is transmitted to the phase calculation section 201.

(S602)

The phase calculation section 201 calculates a phase of motion of the subject 100 based on the measured value of the body motion measurement section 200, and calculates the motion cycle. For example, a maximum value and a minimum value are extracted from the motion waveform shown by the dotted line in FIG. 3. An interval between a time point of the maximum value and a time point of the minimum value is calculated several times, and an average value of the obtained intervals is multiplied by 2 to calculate the motion cycle. The motion cycle calculated by the phase calculation section 201 is transmitted to the condition setting section 203.

(S603)

The condition setting section 203 calculates, based on the motion cycle calculated by the phase calculation section 201, the rotational speed that is one of the imaging conditions. For example, Equation 1 is used for calculation of the rotational speed $\rho$ of the gantry 105. The calculated rotational speed is set as an imaging condition and transmitted to the rotation control section 204.

(S604)

The control section 106 initiates a rotation measurement of the projection images. More specifically, the rotation control section 204 rotates the gantry 105 according to the rotational speed set by the condition setting section 203 so that projection image groups are acquired by the pairs of the X-ray sources 103 and the detectors 104 as the gantry 105 is rotated. It is noted that the body motion measurement section 200 measures the motion of the subject 100 in step with the acquisition of each projection image. The phase calculation section 201 also calculates a phase of the motion of the subject 100 based on the measured values of the body motion measurement section 200. The calculated phase is associated with each projection image.

(S605)

The control section 106 completes the rotation measurement upon the acquisition of the projection images in the angle range required for reconstruction of the tomographic image. That is, the X-ray irradiation from the X-ray source 103 and the rotation of the gantry 105 are stopped.

(S606)

The divide section 202 divides the projection image groups on a phase-by-phase basis based on the motion phases calculated by the phase calculation section 201.

(S607)

The reconstruction section 205 sets a weight based on a phase for reconstruction of the tomographic image. It is noted that a phase of smallest motion amplitude may be selected as the phase for reconstruction of the tomographic image, or alternatively the phase for reconstruction of the tomographic image may be preset by the operator via the input device. If the phase of smallest motion amplitude is selected, weights as shown by the solid lines in FIG. 3 are set.

(S608)

The reconstruction section 205 reconstructs the tomographic image by use of the projection image groups multiplied by the weights set in S607. That is, by using the weights illustrated by the solid lines in FIG. 3, only the projection image groups corresponding to the phase of smallest motion amplitude are used to reconstruct the tomographic image, resulting in minimized artifacts caused by motion.

By virtue of the processing flow described above, the first projection image group and the second projection image group which are placed in the same phase are acquired to mutually compensate for each other's spacing between projection angles. This enables a reduction in artifacts in the tomographic image of the subject 100 including the cyclically moving object to be treated.

Figure 7:
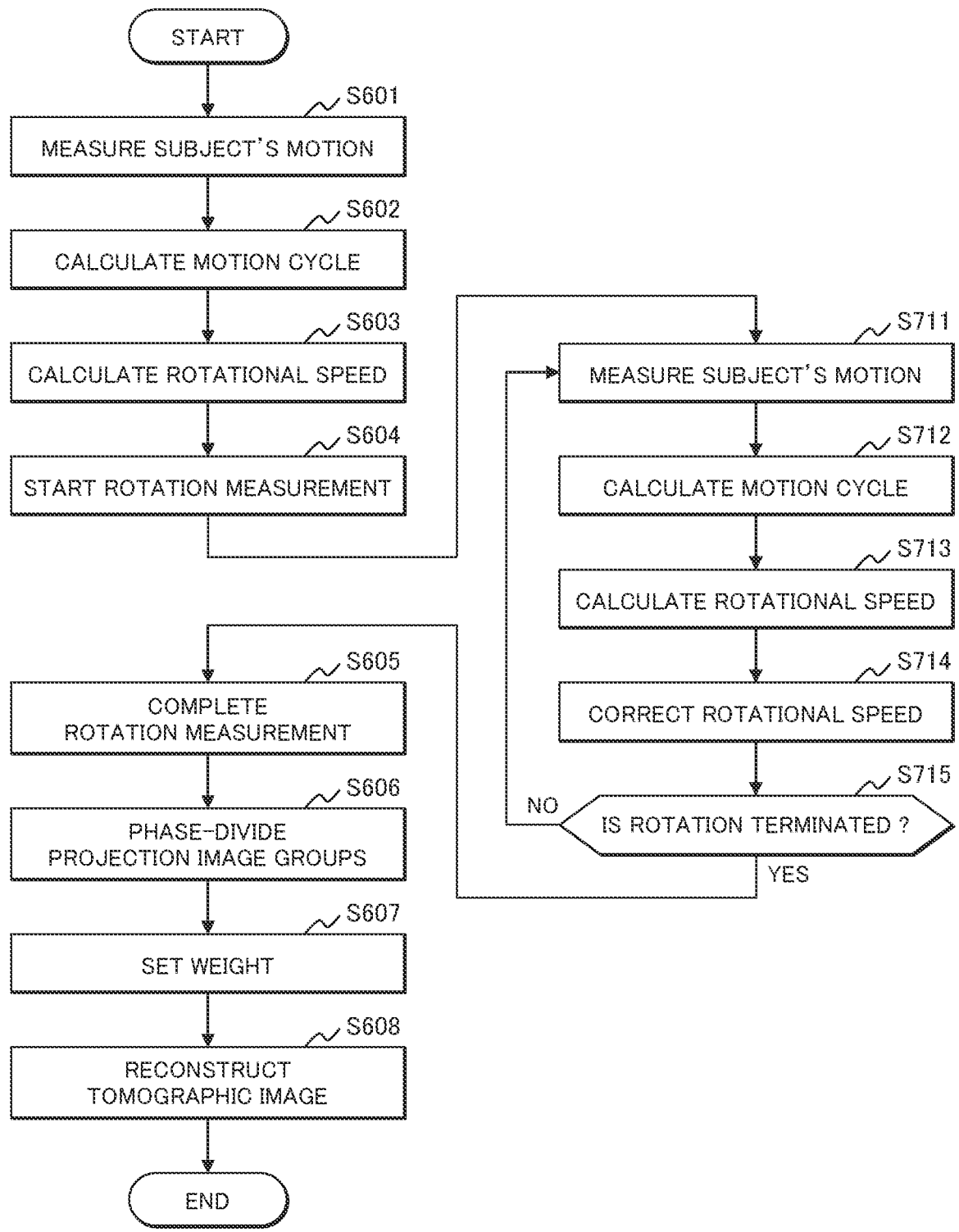
FIG. 7 is a diagram illustrating another example processing flow in Example 1.

Reference is made to FIG. 7 to describe another example processing flow executed in this example, i.e., describe the rotational speed of the gantry 105 being changed in response to a change of the motion of the subject 100 during the rotation measurement. Incidentally, the processing from S601 to S608 is the same as those in FIG. 6 and a description is omitted.

(S711)

The body motion measurement section 200 measures the motion of the subject 100 during the rotation measurement. The measured value obtained by the body motion measurement section 200 is transmitted to the phase calculation section 201.

(S712)

The phase calculation section 201 calculates a phase of the motion of the subject 100 based on the measured value of the body motion measurement section 200, and calculates a motion cycle. The motion cycle calculated by the phase calculation section 201 is transmitted to the condition setting section 203.

(S713)

The condition setting section 203 calculates the rotational speed of the gantry 105 using, e.g., Equation 1, based on the motion cycle calculated by the phase calculation section 201. The calculated rotational speed is set as the imaging conditions and transmitted to the rotation control section 204.

(S714)

If there is a change in motion of the subject 100, for example, if a difference between the motion cycles calculated in S602 and S712 is significantly large, the rotation control section 204 corrects the rotational speed of the gantry 105. It is noted that, while the rotational speed is being increased/decreased, the X-ray irradiation from the X-ray source 103 is stopped.

(S715)

The control section 106 determines based on the angle range of the acquired projection images whether or not the rotation of the gantry 105 should be terminated. If the projection images in the angle range required for reconstruction of the tomographic image are acquired, the processing goes to S606, and if it is not acquired, the processing goes back to S711.

By virtue of the processing flow described above, even if a change in motion of the subject 100 occurs during the rotation measurement, the first projection image group and the second projection image group which are placed in the same phase are acquired to implement mutual compensation for each other's spacing between projection angles, which thus enables a reduction in artifacts in the tomographic image.

Example 2

The description in Example 1 has been given of the case where a weight used for reconstructing the tomographic image has a rectangular waveform. If the weight has a rectangular waveform, discontinuity of the projection images may cause occurrence of artifacts. In this example, the case where the weight has a continuous waveform in the projection angle direction will be described. It is noted that like reference signs are used to indicate components with the same functionality as Example 1, and a description is omitted.

A waveform of a weight according to this example is described with reference to FIG. 8. It is noted that FIG. 8(a) illustrates a weight waveform set based on a waveform with the inverse of the amplitude of the waveform of the motion of the subject 100, and FIG. 8(b) illustrates a weight waveform set by approximating the inverse of the waveform of the motion of the subject 100 by a trigonometric function and/or the like.

The weight waveform illustrated in FIG. 8(a) is a waveform normalized such that the inverse of the motion waveform has a value in a range in which the maximum value is 1.0 and the minimum value is around 0.0, i.e., the influence of the motion can be reduced. For the sake of comparison, in FIG. 8(a), the motion waveform is shown by the dotted line and the weight in FIG. 3 is shown by the broken lines. As illustrated in FIG. 8(a), the weight has a continuous waveform in the projection angle direction, thereby enabling a reduction in artifacts caused by discontinuity of the projection images. Using the weight associated with the motion of the subject 100 also enables a reduction in artifacts caused by the motion.

The weight waveform illustrated in FIG. 8(b) is a weight waveform set by approximating the inverse of the motion waveform by a trigonometric function. For the sake of comparison, in FIG. 8(b), the reverse of the motion waveform is shown by the dotted line and the weight in FIG. 3 is shown by the broken lines. Where an approximate waveform as illustrated in FIG. 8(b) is used, the weight is set by a mathematical expression. Therefore, even if an abrupt motion change occurs in the subject 100, the influence thereof can be inhibited to avoid the risk of the weight representing an abnormal value. Because of the continuous motion waveform in the projection angle direction, a reduction in artifacts caused by discontinuity of the projection images can be achieved. It is noted that an expression used for approximation may be a polynomial expression other than a trigonometric function.

Reference is made to FIG. 9 to illustrate a difference between ranges of projection angles in the rotation measurement. It is noted that FIG. 9(a) illustrates the case the projection angle range in the rotation measurement is 110 degrees and FIG. 9(b) illustrates the case it is 180 degrees, in which the weight of the detector 104a is shown by the solid lines and the weight of the detector 104b is shown by the dotted lines. It is noted that Δθ=90 degrees, and the weight of the detector 104b beyond the projection angle of 180 degrees corresponds to the weight beyond the projection angle of zero degrees.

In FIG. 9(a), in vicinity of the projection angles of zero degrees and 90 degrees, the weight of the detector 104a and the weight of the detector 104b mutually compensate for each other's spacing between projection angles, so that the lack of projection images may be compensated. Further, in FIG. 9(b), throughout the projection angle range, the weight of the detector 104a and the weight of the detector 104b mutually compensate for each other's spacing between projection angles, so that the lack of projection images is compensated. That is, expanding the projection angle range in the rotation measurement enables a reduction in artifacts caused by the lack of projection images.

It is noted that in the description in Example 1, the X-rays are emitted at all projection angles to acquire the projection images, and of the acquired projection image groups, only projection image groups corresponding to a certain phase are used to reconstruct a tomographic image. The projection images that are not used to reconstruct a tomographic image consume the capacity of the storage device and become a factor in increasing wasted radiation exposed to the subject 100. As a result, the projection angle range in which the projection images are acquired is preferably limited. To this purpose, the X-ray irradiation may be performed based on the weights illustrated in FIG. 3 and FIG. 8 to limit the projection angle range in which the projection images are acquired.

Also, the imaging conditions set by the condition setting section 203 are not limited to the rotational speed calculated by Equation 1 and the X-ray irradiation timing calculated by Equation 2. For example, based on the motion cycle T of the subject 100 and the rotational speed ρ of the gantry 105, an angle Δθ to be formed by the pair of the X-ray source 103a and the detector 104a and the pair of the X-ray source 103b and the detector 104b may be set as the imaging conditions. A calculation for the angle Δθ to be formed is made by the following derived from Equation 1.

$$\Delta\theta = T \cdot \rho \cdot (2n-1)/2 \qquad \text{(Eq. 3)}$$

where n is a natural number. The angle Δθ to be formed is set to a value calculated by Equation 3, so that the first projection image group and the second projection image group which are placed in the same phase are acquired to implement mutual compensation for each other's spacing between projection angles, which in turn enables a reduction in artifacts in the tomographic image.

Further, based on a cycle T calculated from the angle Δθ formed by the pair of the X-ray source 103a and the detector 104a and the pair of the X-ray source 103b and the detector 104b and from the rotational speed ρ of the gantry 105, the timing for urging the subject 100 to breathe may be displayed. It is noted that the following derived from Equation 1 is used to calculate the cycle T.

$$T = 2\Delta\theta/(\rho \cdot (2n-1)) \qquad \text{(Eq. 4)}$$

Based on the cycle T calculated by Equation 4, the subject 100 is urged to breathe, which allows the first projection image group and the second projection image group that are placed in the same phase to be acquired to implement mutual compensation for each other's spacing between projection angles. Thus, a reduction in artifacts in the tomographic image is achieved.

It should be understood that the radiographic imaging device and the radiographic treatment device according to the present invention are not limited to the above examples and may be embodied by making modifications to the elements without departing from the scope and spirit of the present invention. Further, a plurality of elements disclosed in the above examples may be combined as appropriate. Further, some of all the elements disclosed in the above examples may be omitted.

REFERENCE SIGNS LIST

100 . . . subject,
101 . . . treatment radiation source,
102 . . . bed,
103 . . . X-ray source, 104 . . . detector,
105 . . . gantry,
106 . . . control section,
200 . . . body motion measurement section,
201 . . . phase calculation section,
202 . . . divide section,
203 . . . condition setting section,
204 . . . rotation control section,
205 . . . reconstruction section.

The invention claimed is:

1. A radiographic imaging device comprising:
a gantry that is equipped with two sets of radiation sources from which radiation is emitted to a subject and detectors that detect the radiation passing through the subject, the radiation sources and the detectors being used in pairs, the gantry rotating the radiation sources and the detectors around the subject; and
a central processing unit (CPU) configured to:
reconstruct a tomographic image of the subject based on multiple projection images generated from output of the detectors,
calculate a plurality of motion phases based on cyclic motion of the subject,
divide, on a phase-by-phase basis, first projection image groups of multiple projection images acquired by the first set of the two sets, and second projection image groups of multiple projection images acquired by the second set of the two sets,
set a rotational speed of the gantry as an imaging condition such that a first projection image group of the first projection image groups and a second projection image group of the second projection image groups mutually compensate for spacing between respective projection angles of the first set of radiation sources and the second set of radiation sources, the first projection image group and the second projection image group being in a same phase, and
reconstruct the tomographic image by use of the first projection image group and the second projection image group that are in the same phase.

2. The radiographic imaging device according to claim 1, wherein the rotational speed is set based on a cycle of the motion and an angle formed by the first set and second set of radiation sources and detectors.

3. The radiographic imaging device according to claim 1, wherein the CPU is configured to set an irradiation timing of radiation as an imaging condition, and
wherein the irradiation timing is set based on a cycle of the motion.

4. The radiographic imaging device according to claim 1, wherein the CPU is configured to set a projection angle range of each projection image to allow the first projection image group and the second projection image group that are placed in the same phase, to implement mutual compensation for the spacing between the respective projection angles.

5. The radiographic imaging device according to claim 1, wherein the CPU is configured to set a projection angle range of each projection image to create a partial overlap between the first projection image group and the second projection image group that are placed in the same phase.

6. The radiographic imaging device according to claim 1, wherein the imaging conditions include an angle formed by the first set and second set of radiation sources and detectors, and
wherein the angle formed is set based on a cycle of the motion and a rotational speed of the gantry.

7. The radiographic imaging device according to claim 1, further comprising a display device to display timing for urging the subject to breathe,
wherein the timing is set based on an angle formed by the first set and second set of radiation sources and detectors and a rotational speed of the gantry.

8. A radiographic treatment device, comprising:
the radiographic imaging device according to claim 1; and
a treatment radiation source from which treatment radiation is emitted to an object to be treated within the subject.

9. The radiographic imaging device according to claim 2, wherein when the angle formed is $\Delta\theta$, the cycle is T, and a natural number is n, the rotational speed $\rho$ is expressed by $\rho = 2\Delta\theta/(T \cdot (2n-1))$.

10. The radiographic imaging device according to claim 3, wherein when the cycle of the motion is T, the irradiation timing t of radiation is expressed by $t = 2T/(2n-1)$.

* * * * *